United States Patent [19]
Sugden et al.

[11] Patent Number: 5,194,601
[45] Date of Patent: Mar. 16, 1993

[54] LYTIC ORIGIN OF REPLICATION FOR EPSTEIN-BARR VIRUS (EBV)

[75] Inventors: William M. Sugden; Wolfgang Hammerschmidt, both of Madison, Wis.

[73] Assignee: Wisconsin Alumni Research Foundation, Madison, Wis.

[21] Appl. No.: 409,843

[22] Filed: Sep. 18, 1989

[51] Int. Cl.$^5$ .................... C12N 15/38; C12N 15/64; C12N 7/00

[52] U.S. Cl. .................... 435/320.1; 435/172.1; 435/235.1; 435/172.3; 935/27; 935/32; 536/23.5

[58] Field of Search .................. 435/320.1, 259, 235.1; 536/27; 935/31, 32, 27

[56] References Cited

U.S. PATENT DOCUMENTS 4,686,186  8/1987  Sugden et al. ..................... 435/243

OTHER PUBLICATIONS

B. Sugden, et al., 23 J. Vir. 503-508 (1977).
C. Kintner, et al., 17 Cell 661-671 (1979).
B. Sugden, et al., 83 J. Inv. Derm. 82s-87s (1984).
J. Yates, et al., 81 P.N.A.S. USA 3806-3810 (1984).
J. Yates, et al., 313 Nature 812-815 (1985).
D. Reisman, et al., 6 Mol. and Cell. Bio 3838-3846 (1986).
V. Baichwal, et al., 61 J. Vir. 866-875 (1987).
W. Hammerschmidt, et al., 62 J. Vir. 1355-1363 (Apr. 1988).
B. Hirt, 26 J. Mol. Biol. 365-369 (1967).
H. zur Hausen, et al., 272 Nature 373-375 (1978).
K. Jeang, et al., 48 J. Vir. 135-148 (1983).
J. Countryman, et al., 82 P.N.A.S. USA 4085-4089 (1985).
L. Heston, et al., 295 Nature 160-163 (1982).
R. Baer, et al., 310 Nature 207-211 (1984).
K. Takada, et al., 57 J. Vir. 1016-1022 (1986).
J. Knutson, et al., 164 Anal. Biochem. 44-52 (1987).
M. Cho, et al., 51 J. Vir. 199-207 (1984).
A. Polack, et al., 27 Gene 279-288 (1984).
G. Laux, et al., 56 J. Vir. 987-995 (1985).
A. Chevallier-Greco, et al., 5 EMBP J. 3243-3249 (1986).
J. Yates, et al., Cancer Cells 6/Eukaryotic DNA Replication 197-205, Cold Spring Harbor. (1988).
D. Vlazny, et al., 78 P.N.A.S. USA 742-746 (1981).
R. Spaete, et al., 30 Cell 295-304 (1982).
N. Stow, et al., 130 Vir. 427-438 (1983).
B. Roizman, et al., Herpes Virus And Their Replication, Virology, B. N. Fields, et al., ed. Raven Press, N.Y. 497-526 (1985).
M. DePamphilis, et al., 52 Cell 635-638 (Mar. 1988).
S. Deb. et al., 62 J. Vir. 2516-2519 (Jul. 1988).
W. Hammerschmidt, et al., 55 Cell 427-433 (Nov. 1988) (not prior art).

*Primary Examiner*—David L. Lacey
*Assistant Examiner*—T. Michael Nisbet
*Attorney, Agent, or Firm*—Quarles & Brady

[57] ABSTRACT

The invention provides lymphotrophic herpes virus (preferably EBV) recombinants. The portions of the virus that are responsible for the packaging and lytic phase replication have been isolated and cloned. When used with vectors and hosts containing a segment that controls plasmid replication, they provide a means of carrying foreign genes into B-lymphocytes.

1 Claim, 1 Drawing Sheet

LYTIC ORIGIN OF REPLICATION FOR EPSTEIN-BARR VIRUS (EBV)

This invention was made with United States government support awarded by the NIH, Grant #(s): P01-CA22443 and P30-CA07175. The United States Government has certain rights in this invention.

BACKGROUND OF THE INVENTION

A. Field Of The Invention

The present invention relates to recombinant DNA technology. It is especially useful for allowing the production of Epstein-Barr virus vectors capable of carrying foreign genes into B-lymphocytes.

B. Description Of The Art

Although some progress has been made in using recombinant-DNA techniques to carry foreign genes into certain eukaryotic hosts (e.g. using retrovirus vectors), it is of particular interest to develop vector systems that are specially suited for use with B-lymphocytes. Apart from pure research applications, this would enhance the ability to produce foreign proteinaceous materials in B-lymphocytes (e.g. where lymphocytes are a host of choice), and/or permit the development of drugs that interact with B-lymphocytes.

EBV is a human herpes virus of the gamma herpesviridae subfamily that infects and immortalizes B-lymphocytes in vitro. It is one of the lymphotrophic herpes viruses. Its viral DNA is usually maintained as complete multiple copies of plasmids in these immortalized cells. An origin of plasmid replication, oriP, is the only element required in cis for EBV plasmid replication. This was the subject of U.S. Pat. No. 4,686,186 (the disclosure of this patent and of all articles referred to herein are incorporated by reference as if fully set forth). These immortalized cells are said to be "latently" infected by EBV because only a few viral genes are usually expressed in them, and virion structural (packaging) genes are not among these normally expressed genes.

Under unusual circumstances (e.g. induction) viral gene expression can change dramatically to yield the "lytic" phase of the EBV life cycle. Most or all of the 90–100 viral genes are expressed during the lytic phase, and the viral DNA is amplified by a replication mechanism distinct from that used to maintain the viral DNA during its latent phase of infection.

Because of these factors, EBV is of interest as a potential vector system. However, there exists in nature no identified host cell which normally supports a lytic infection by this natural herpes virus. Moreover, the viral DNA (which is 172 kbp in length) is too large to permit engineering in vitro with the goal of introducing the mutant genomes into recipient cells. Also, primary human B-lymphocytes which are the natural host for infection with EBV are both intractable in culture and recalcitrant to DNA transfection. Thus, it can be seen that a need has existed for developing means of using EBV recombinants to carrying foreign genes into eukaryotic cells (such as B-lymphocytes).

SUMMARY OF THE INVENTION

In one form, the invention provides a recombinant vector having a first segment from a lymphotrophic herpes virus. This segment has a function in nature of mediating viral lytic phase replication. The vector also has a foreign eukaryotic gene component linked as part of the recombinant vector.

The recombinant vector is preferably a plasmid which also has a sequence from another plasmid which is not a lymphotrophic herpes virus sequence and which facilitates the replication of the recombinant plasmid in a prokaryotic host. The plasmid vector can also have a second segment from a lymphotrophic herpes virus, the second segment having the function in nature of assisting in maintaining a plasmid as a plasmid.

The recombinant vector can, if desired, have viral packaging sequences from a lymphotrophic herpes virus, and it can be an infectious virus (instead of a plasmid). The preferred lymphotrophic herpes virus is Epstein-Barr virus.

In another aspect of the invention, there is provided a recombinant eukaryotic host which is non-living and/or non-human, and which is capable of producing recombinant lymphotrophic herpes virus that can infect a human B-lymphocyte. The virus so produced preferably contains a segment from a lymphotrophic herpes virus and an expressable foreign eukaryotic gene. The preferred virus is Epstein-Barr virus.

It will be appreciated that the inventors have located those minimal lymphotrophic herpes virus sequences needed in cis for infectious viral production, and discovered how to use them to form recombinants that result in infectious recombinant viral vectors.

The objects of the invention therefore include:

A. providing a recombinant vector of the above king;
B. providing a eukaryotic host of the above kind; and
C. providing infectious virus of the above kind.

These and still other objects and the advantages of the present invention will be apparent from the description that follows.

DESCRIPTION OF THE PREFERRED EMBODIMENTS

General Overview

Figure 1:
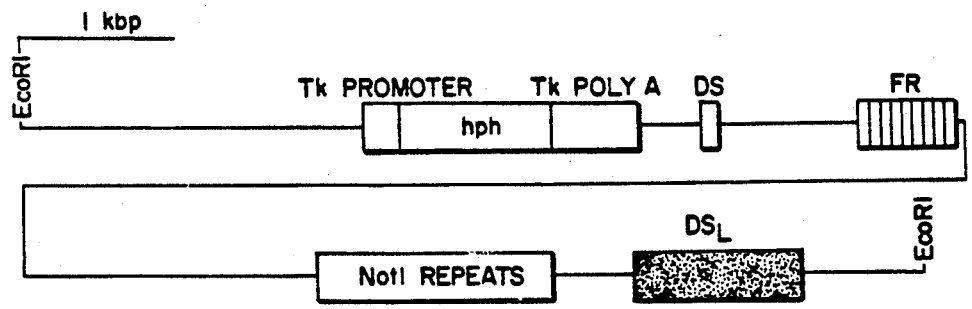
FIG. 1 depicts the structure of p562, a plasmid containing oriLyt.

We have searched the EBV genome functionally for an origin of DNA replication that mediates replication during the "lytic phase" of the viral life cycle. The lytic phase origin (oriLyt) governs viral replication, whereas the previously located oriP governs means for replicating the plasmid copies (see U.S. Pat. No. 4,686,186 with respect to oriP). The lytic phase can be induced in some cells lines latently infected with EBV by treating the cells with 12-O-tetradecanoyl-phorbol-13-acetate (TPA), or sodium butyrate, or by introduction of a vector expressing the BZLF-1 gene of EBV. See generally H. zur Hausen et al., 272 Nature 373–375 (1978); J. Countryman et al., 82 P.N.A.S. 4085–4089 (1985); K. Takada et al., 57 J. Virol 1016–22 (1986).

A complete set of fragments encompassing the EBV genome has been introduced individually along with a vector expressing BZLF-1 into a cell line latently infected with EBV, and the fragments were assayed subsequently for their capacity to replicate. We have found that one region of EBV DNA that is present twice in the genome of most isolates of EBV serves as a lytic origin of replication (oriLyt).

We then combined the two functionally distinct origins of DNA replication of EBV, oriP and oriLyt in a plasmid, and introduced this vector into a cell line latently infected by EBV. The latently infected cells maintain this two-origin vector as a plasmid at approximately ten molecules per cell. When the lytic life cycle of EBV in these cells was switched on by introducing an induction source (e.g. a vector expressing the BZLF-1 gene), the two-origin vector was amplified 100- to 1000-fold to yield head-to-tail viral concatemers (precursors of the virus). This work was described in more detail in our article W. Hammerschmidt et al., 55 Cell 427–33 (November 1988) (not prior art).

We next searched for sequences coding for cleaving and packaging functions. During the lytic phase naturally occurring EBV synthesizes DNAs as long concatemers which are ultimately cleaved to genomic-sized pieces that can be packaged to form the virus. A 3 kbp fragment containing the fused LTR termini ("TR") from a circular molecule of EBV DNA was cloned into a plasmid containing oriLyt and oriP. This plasmid, p554[TR+], was introduced into a cell line latently infected with EBV (a helper cell line) and the lytic phase of the viral life cycle was induced by exposing the plasmid to TPA. After four days the cell-culture supernatant was collected and it tested positive for encapsidated virus. Thereafter, the encapsidated virus was used to infect B-lymphocytes.

oriLyt

To search for a lytic origin of EBV, oriLyt, we assayed for the replication of recombinant DNAs in cells supporting the lytic phase of the viral life cycle. D98/HR1 cells that maintain EBV latently were co-electroporated with each member of a set of recombinant plasmids (see B. Sugden et al., 83 J. Invest. Dermatol. 82s-87s (1984)) encompassing the entire genome of the EBV strain B95-8 and the plasmid pCMV-BZLF-1. pCMV-BZLF-1 induced the lytic phase of the viral life cycle in recipient cells. Four days after electroporation, DNA was prepared from the treated cells (see B. Hirt, 26 J. Mol. Biol. 365-369 (1967)), first cleaved with BamHI, and the cleaved with DpnI. The cleaved DNAs were separated on agarose gels, transferred to membranes, and detected by nucleic acid hybridization using prokaryotic vector DNA sequences as a probe. See W. Hammerschmidt et al., 55 Cell 427–433 (1988) (not prior art) for more details.

To define oriLyt more closely we undertook a deletion analysis of the DNA shared by various plasmids. Progressive deletions from each end as well as internal deletions were generated. The resulting sequences were tested for their ability to support replication.

Nucleotides 52,623–52,944 and nucleotides 53,207–53,581 comprise a minimally functional oriLyt (using the numbering code of R. Baer et al., 310 Nature 207-211 (1984)). It appears that EBV has two copies of oriLyt, but that only one copy is required for viral lytic phase replication.

Construction Of An oriP/oriLyt Vector

We have discovered that our oriLyt lies approximately 40 kbp away from oriP on the EBV genome. We therefore constructed a vector, p562, which contains oriP and oriLyt separated by approximately 6 kbp of foreign DNA (see FIG. 1) to determine whether such recombinant vectors could be maintained in a cell latently infected with EBV and then be amplified upon induction of the lytic cycle within the host cell. We analyzed the structure of the amplified DNA to determine whether it is composed of parent-length plasmids (as are the products of replication mediated by oriP) or whether it contains concatemeric molecules.

As shown in FIG. 1, oriP encompasses a dyad symmetry element (DS) and a family of 30 bp repeats (FR). A foreign test gene (hygromycin-B resistance gene) is flanked by transcriptional signal sequences (promoter and polyadenylation signal) of the HSV-1 thymidine kinase (TK) gene.

The p562 vector, which therefore encodes resistance to hygromycin-B, was introduced in the EBV-positive cell line GG68 (L. Heston et al., 295 Nature 160–163 (1982)) and a pool of hygromycin-resistant cells was selected. The vector p562 replicates as a plasmid in these cells at approximately ten copies per cell on the average. pCMV-BZLF-1 (see W. Hammerschmidt et al., 55 Cell 427–433 (1988)) was electroporated into these cells, and DNA was prepared 2 and 4 days after induction of the lytic phase.

p562 was amplified several hundred fold in the 10%–20% of the cells that took up pCMV-BZLF-1, and most of the amplified DNA was present in a high molecular weight form consistent with it being concatemerized. Amplification of p562 required the lytic viral gene product, DNA polymerase, because the additional of PAA prevented amplification and concatemerization of p562. Treatment of the host cells with PAA did not apparently diminish plasmid replication mediated by oriP, nor did it block proliferation of the cell population as a whole.

Packaging

A 3 kbp fragment containing the fused termini from a circular molecule of EBV DNA was cloned into a plasmid containing oriLyt. These termini are composed of variable numbers of direct repeats termed "terminal repeats" (TR). A parental TR− plasmid and the derivative p554[TR+] (see FIG. 2) carrying the fused termini were separately introduced into a cell line latently infected with EBV and the lytic phase of the viral life cycle was induced (e.g. by the addition of 20 ng TPA/ml to the tissue culture medium). After four days the cell-culture supernatant was collected and probed for encapsidated DNA and the resulting signal was compared with signals arising from the plasmid-derived DNAs within the cells. Only the plasmid p554[TR+], which contains the terminal repeat region of EBV, was encapsidated into virions such that its DNA was detectable in the supernatant of the induced cells. These encapsidated derivatives of p554[TR+] probably consist of six head-to-tail copies of the parent p554[TR+].

Figure 2:
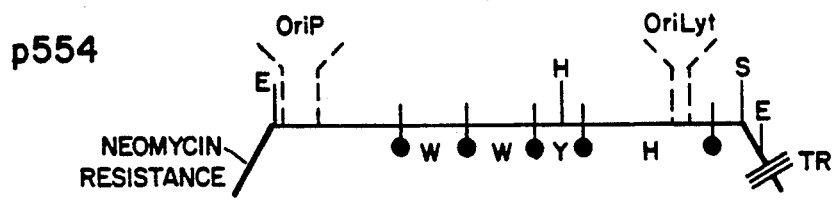
FIG. 2 depicts the structure of p554, a plasmid containing both oriLyt and packaging coding sequences.
Figure 3:
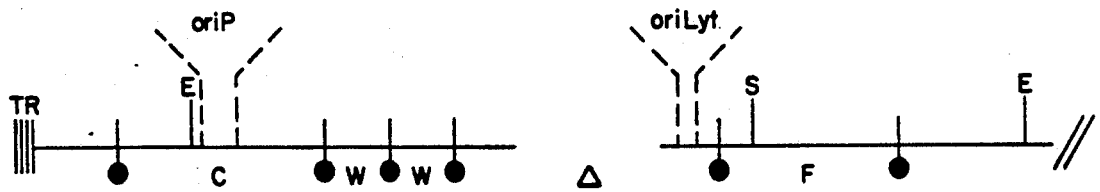
FIG. 3 depicts the helper viral sequence P3HR1 which is defective, yet supplies needed trans constituents.

The structure of a linear form of a P3HR1 viral DNA and the sequence of the p554 plasmid DNA are diagrammed in FIGS. 2 and 3. The vertical lines marked with TR represent the terminal repeats. OriP and oriLyt represent respectively the origins of plasmid and lytic replication of EBV. The gap in P3HR1 DNA denoted with a triangle indicates a deletion within P3HR1 DNA which removes the last two exons of EBNA-LP and all of EBNA-2 open reading frame. The letters above the depicted DNAs indicate sites of cleavage by different endonucleases: E (EcoRI); S (SalI); H (HindIII). The inverted lollypops indicate sites of cleavage by BamHI and the letters below the depicted DNAs between the lollypops denote the names of different BamHI cleavage products of EBV. The thickened lines in p554 represent vector sequences derived from pKan-2, J. Yates et al., 81 P.N.A.S. 3806-3810 (1981) which among other things contains a foreign expressed test gene coding for neomycin resistance.

Use As A Vector

In order to determine whether packaged DNAs derived from transfected plasmids are infectious, we examined whether they could rescue immortalization by the above described EBV strain, termed P3HR1, which by itself was not able to immortalize human primary B-cells. The P3HR1 strain of EBV is a variant carried in a cell line selected by screening clones of a Burkitt's lymphoma cell line for virus production. See Y. Hinuma et al., 1 J. Virol. 1203-1206 (1967). P3HR1 lacks the last two exons of the EBNALP (EBV nuclear antigen-leader protein) gene and all of the EBNA-2 (EBV nuclear antigen-2) gene (K.-T, Jeang et al., 48 J. Virol. 135-148 (1983)).

The plasmid p554[TR+] contains all of the EBNA-LP and EBNA-2 DNA sequences deleted in the P3HR1 strain of EBV. p554[TR+] was introduced into the cell line which contains the P3HR1 strain of EBV (the cell line is also termed P3HR1 ) and the lytic phase of the viral life cycle induced by cotransfection with the viral transactivating gene, BZLF-1. The virus stock released from these induced cells consists of the endogenous P3HR1 virus, encapsidated concatemers of p554[TR+], and possible recombinants between them. Separately, the P3HR1 cell line was induced to generate a stock of virus consisting only of the endogenous P3HR1 virus. These two stocks of virus were used to infect primary human B-hymphocytes. The virus stock derived from P3HR1 plus p554[TR+] immortalized infected B-lymphocytes; that from P3HR1 alone did not.

As stated above, the plasmid p554 contains the plasmid origin of replication, oriP, of EBV. A concatemer of p554 could therefore replicate as a plasmid after circularization in cells if the EBNA-1 gene of EBV were provided in trans. EBNA-1 is the only protein encoded by EBV which is required for plasmid replication (see U.S. Pat. No. 4,686,186). The P3HR1 strain of EBV encodes EBNA-1 and could provide it in trans to a concatemric derivative of p554 such that both the P3HR1 and concatemeric p554 DNAs could be maintained as plasmids in cells.

The finding that some B-lymphocytes were immortalized by the combination of the endogenous P3HR1 virus and a defective virus derived from p554 indicates that foreign DNAs can now be introduced into primary human B-lymphocytes.

EXAMPLE

The plasmids p135 and p554 were introduced in a GG68 clone of P3HR1 cells by electroporation. p135 contains the contiguous EBV DNA sequences of the B958 strain which lie between the EcoRI site at 7315 and the SalI site at 56,081 inserted into the vector, pkan 2 (J. Yates et al., 313 Nature 812-815 (1985)), but has only two copies of the BamHI W fragment. p554 was derived from it by inserting the region of terminal repeats of EBV found between an XhoI site at 169,423 and a SalI site at 644 into a unique NruI site in p135 upstream of the TK promoter within the pkan 2 vector sequences. 10 $\mu$g of each plasmid DNA was introduced into $10^7$ cells. Pools of cells carrying these DNAs were selected by propagating the cells in 1500 $\mu$g/ml of G418. Since p135 and p554 carry the plasmid origin of DNA replication (oriP) of EBV they can replicate as plasmids in these cells. The lytic phase of the life cycle of the endogenous EBV was induced in resistant cells by TPA (20 ng/ml) and n-butyrate (3 mM) which also supports the amplification of the introduced p135 and p554 DNAs.

Four days after electroporation, the cells and supernatants were harvested. Virus was pelleted from the supernatants by ultracentrifugation and treated with DNAse to destroy any non-encapsidated DNA. Cellular and viral DNAs were isolated, cleaved with BamHI, electrophoresed in 0.7% agarose gels, transferred to a nylon membrane and detected by hybridization with a radiolabelled probe of pKan 2 (J. Yates et al., 313 Nature 812-815 (1985)). Molecular markers consisting of a BstEII digest of lambda DNA were used but are not shown.

A culture of p554 in *E. Coli* cells is on deposit at the American Type Culture Collection, Rockville, Md., U.S.A., with ATCC number 67982. It will be made available upon issuance of this patent and as provided under U.S. and other applicable patent laws. However, this availability is not to be construed as a license to use the invention.

To isolate the plasmid from this deposited cell line one follows the protocols described in detail in Molecular Cloning, A Laboratory Manual, T. Maniatis et al. (Cold Spring Harbor, N.Y.) (1982).

To insert a foreign gene of interest in p554 one inserts the gene with an appropriate promoter and polyA at the unique Sal I ("S") site shown in FIG. 2 using standard techniques.

To enter the lytic phase with the modified p554 one introduces the modified p554 into P3HR1 cells using electroporation techniques as described in detail by Knutson et al., 164 Anal. Biochem. 44-52 (1987). See also Y. Hinuma et al.. 1 J. Virol. 1203-1206 (1967) for P3HR1. These cells are also commercially available as ATCC HTB62. After electroporation, the cells are treated with 20 ng of TPA/ml in tissue culture medium and the system is stored at 37° C. for four days.

To harvest the packaged virus, one pellets the cells four days after introducing the above plasmid in a low speed centrifuge. One then harvests the supernate and filters it through a 0.1 micron sterile filter. The resulting virus stock is maintained at 4° C.

To infect a eukaryotic cell (e.g. human B-lymphocyte with the virus) one can expose $10^6$ B-lymphocytes at 25° C. and then plate the infected cells as described in B. Sugden et al., 25 J. Virol. 503-508 (1977). It will be appreciated that viral gene products needed in trans for replication and packaging can be provided by the induced, endogenous EBV helper virus, or by a defective helper virus.

While the preferred form of the invention has been discussed using the example of EBV, the invention may also be appliable to other lymphotrophic herpes viruses as well. Also, while test systems have used antibiotic resistance genes as the "foreign gene", the foreign genes might also be those of interest for research purposes (e.g. oncogenes), or those of commercial value (e.g. use the B-lymphoblast as a production host in vivo) or those needed to regulate cell functions (e.g. a drug). Further, while human primary B-lymphoblasts are the preferred host, other eukaryotic host cells could provide suitable hosts as well. Thus, the invention is not to be limited by the illustrative embodiments described above. Instead, the invention is to be judged by the claims which follow.

We claim:

1. A recombinant plasmid vector comprising:
   a first segment from a lymphotrophic herpes virus, the segment having a function of mediating viral lytic phase replication;
   a foreign expressible gene component from other than a lymphotrophic herpes virus; and
   a second segment from a lymphotrophic herpes virus, the second segment having a function of mediating latent phase plasmid replication if the recombinant plasmid is inserted into a eukaryotic host that has been transformed by the lymphotrophic herpes virus.

* * * * *